United States Patent
Woll et al.

(10) Patent No.: US 7,632,277 B2
(45) Date of Patent: Dec. 15, 2009

(54) ORTHOPEDIC INTRAMEDULLARY FIXATION SYSTEM

(75) Inventors: Christian Woll, Littleton, MA (US); Duane Dickens, San Clemente, CA (US); Richard Woods, Littleton, MA (US)

(73) Assignee: Woll Bioorthopedics LLC, Littleton, MA (US)

( * ) Notice: Subject to any disclaimer, the term of this patent is extended or adjusted under 35 U.S.C. 154(b) by 876 days.

(21) Appl. No.: 10/811,661

(22) Filed: Mar. 29, 2004

(65) Prior Publication Data

US 2005/0216007 A1   Sep. 29, 2005

(51) Int. Cl.
A61F 5/00   (2006.01)
(52) U.S. Cl. .................................... 606/86 R
(58) Field of Classification Search .......... 606/60, 606/62–68, 105; 623/1.12; 411/34
See application file for complete search history.

(56) References Cited

U.S. PATENT DOCUMENTS

| | | | |
|---|---|---|---|
| 3,760,802 A | | 9/1973 | Fischer et al. |
| 3,779,239 A | | 12/1973 | Fischer et al. |
| 4,091,806 A | | 5/1978 | Aginsky |
| 4,227,518 A | | 10/1980 | Aginsky |
| 4,236,512 A | | 12/1980 | Aginsky |
| 4,237,875 A | | 12/1980 | Termanini |
| 4,275,717 A | | 6/1981 | Bolesky |
| 4,289,124 A | | 9/1981 | Zickel |
| 4,365,624 A | | 12/1982 | Jaquet |
| 4,453,539 A | | 6/1984 | Raftopoulos et al. |
| 4,480,637 A | | 11/1984 | Florek |
| 4,535,763 A | | 8/1985 | Jaquet |
| 4,632,101 A | | 12/1986 | Freedland |
| 4,640,271 A | | 2/1987 | Lower |
| 4,752,168 A | * | 6/1988 | Richter .................. 411/38 |
| 4,808,163 A | * | 2/1989 | Laub ..................... 604/105 |
| 4,862,883 A | | 9/1989 | Freeland |
| 4,862,891 A | * | 9/1989 | Smith ..................... 606/191 |
| 4,964,403 A | | 10/1990 | Karás et al. |
| 5,002,543 A | | 3/1991 | Bradshaw et al. |
| 5,053,035 A | | 10/1991 | McLaren |
| 5,057,103 A | | 10/1991 | Davis |
| 5,658,310 A | | 8/1997 | Berger |

(Continued)

FOREIGN PATENT DOCUMENTS

DE   1810799   6/1970

(Continued)

*Primary Examiner*—Thomas C Barrett
*Assistant Examiner*—Michael J Araj
(74) *Attorney, Agent, or Firm*—Dalina Law Group PC (57) ABSTRACT

A system and method for repairing fractured long bones. A guide wire is inserted through an opening drilled in a proximal bone segment and pushed through the intramedullary cavity of the proximal bone segment, across the fracture site and into the intramedullary cavity of a distal bone segment. A dilator is inserted over the guide wire and pushed through the intramedullary cavity into the distal bone segment to a stop at the distal end of the guide wire. A flexible tube having a radially expandable distal portion is then pushed over the guide wire into the distal bone segment and against the dilator. A compression nut is threaded over the proximal end of the guide wire to engage the proximal bone segment and compress the flexible tube. Compression of the flexible tube deploys the radially expandable distal portion to anchor the device in the distal bone segment.

7 Claims, 9 Drawing Sheets

U.S. PATENT DOCUMENTS

| | | |
|---|---|---|
| 5,810,820 A | 9/1998 | Santori et al. |
| 5,879,352 A | 3/1999 | Filoso et al. |
| 5,928,267 A | 7/1999 | Bonutti et al. |
| 5,968,047 A | 10/1999 | Reed |
| 5,976,137 A | 11/1999 | Mayer |
| 6,146,406 A | 11/2000 | Shluzas et al. |
| 6,261,289 B1 | 7/2001 | Levy |
| 6,277,124 B1 | 8/2001 | Haag |
| 6,315,779 B1 | 11/2001 | Morrison et al. |
| 6,338,732 B1 | 1/2002 | Yang |
| 6,387,096 B1 | 5/2002 | Hyde, Jr. |
| 6,443,954 B1 | 9/2002 | Bramlet et al. |
| 6,517,541 B1 | 2/2003 | Sesic |
| 6,547,792 B1 | 4/2003 | Tsuji et al. |
| 6,554,833 B2 | 4/2003 | Levy et al. |
| 6,565,573 B1 | 5/2003 | Ferrante et al. |
| 6,575,973 B1 | 6/2003 | Shekalim |
| 6,575,974 B2 | 6/2003 | Gotfried |
| 6,575,976 B2 | 6/2003 | Grafton |
| 6,582,453 B1 * | 6/2003 | Tran et al. .................... 606/232 |
| 6,592,587 B1 | 7/2003 | Roger |
| 6,602,259 B1 | 8/2003 | Masini |
| 6,607,531 B2 | 8/2003 | Frigg |
| 6,648,890 B2 * | 11/2003 | Culbert et al. ................ 606/63 |
| 6,652,528 B2 | 11/2003 | Vandewalle |
| 6,676,665 B2 * | 1/2004 | Foley et al. ................. 606/105 |
| 6,736,818 B2 | 5/2004 | Perren et al. |
| 6,746,191 B2 * | 6/2004 | Edland ........................ 411/34 |
| 6,783,530 B1 | 8/2004 | Levy |

FOREIGN PATENT DOCUMENTS

| | | |
|---|---|---|
| DE | 19612276 A1 | 10/1997 |
| GB | 2268068 A | 1/1994 |
| SU | 967478 | 10/1982 |
| WO | WO 97/18769 | 5/1997 |

* cited by examiner

ORTHOPEDIC INTRAMEDULLARY FIXATION SYSTEM

FIELD OF THE INVENTION

This invention relates generally to an orthopedic support system and apparatus and more particularly to an intramedullary (IM) support apparatus and method of use thereof for supporting fractured long bones. The IM support apparatus according to the present invention is minimally invasive and provides improved alignment of bone segments.

BACKGROUND OF THE INVENTION

Various methods and apparatus have long been used for positioning, stabilizing and supporting bone segments to repair bone fractures in humans and animals. Simple external apparatus such as slings and splints are well known and are still used alone or in combination with invasive apparatus to repair broken bones. Slings are used alone in certain circumstances where use of invasive apparatus or implants presents an unacceptable risk of injury to a patient. For example, slings are often used without any invasive apparatus to repair a fractured clavicle because implantation of known invasive bone repair apparatus to repair a fractured clavicle can risk life threatening damage to the patient's subclavian artery or damage to other vessels, nerves, nerve bundles, vital organs or surrounding tissues.

Since invasive repair of a fractured clavicle presents medical risk, patients having a fractured clavicle often forgo the benefits offered by various invasive apparatus and implants. Such benefits which include improved bone segment positioning, stabilizing and support promote more rapid recovery and reduce patient discomfort. Further, use of slings alone often allows misaligned bone segments to heal such that a visibly conspicuous deformation or a weak area remains which is susceptible to re-injury. Accordingly, it would be advantageous to provide a clavicle repair apparatus with reduced risk of injury to the patient.

Known invasive apparatus for bone segment repair include various configurations of bone fracture reduction rods, orthopedic screws, intramedullary nails, intramedullary screws and the like. For example, U.S. Pat. No. 6,338,732 to Yang discloses an in-marrow nail structure having two threaded ends for drilling and engaging fractured bone segments. A nut is screwed over a threaded proximal portion of the structure to apply compressive force to the bone segments. The apparatus disclosed in Yang and similar devices involve installing a drilling tip within the intramedullary cavity. These devices typically incorporate threads having a cutting edge in at least a distal portion whereby drilling is performed by rotating the devices around their longitudinal axis. Accordingly, such devices are typically unsuitable for implantation in curved bone segments. Such devices also present a high risk of drilling through a bone segment into surrounding tissue, and are therefore not well suited for use in repairing a fractured clavicle. It would be desirable to provide an intramedullary apparatus that is suitable for use in curved bone segments without presenting a high risk of damaging surrounding tissue.

In addition to providing a drilling capability for implanting an intramedullary device, the threaded distal portion of some known devices serves as an anchor which secures the distal portion of the device to a distal bone segment. Bone segments are held together by also providing a compressing portion which engages the proximal bone segment and travels toward the anchored distal portion.

In another type of known intramedullary support apparatus, an expandable anchor portion is provided for engaging the distal bone segment. For example, U.S. Pat. Nos. 3,779,239; 3,760,802 and 4,227,518 disclose particular intramedullary retraction nails that include an expansion element in their distal portion. The expansion elements serves as an anchor in a distal bone segment. The aforementioned devices are generally directed toward a rod disposed with a tubular portion. Relative linear motion between the rod and the tubular portion, such as by threading the rod to the tubular portion, causes actuation of the expansion element to engage the bone lining in the distal portion. A bolt head and or nut and washer are installed over or incorporated with the proximal portion of the rod which protrudes from a hole drilled in the proximal bone segment. In the apparatus disclosed in U.S. Pat. Nos. 3,779,239 and 3,760,802 the central rod is curved to correspond with the curvature of the bone under repair.

Installation of a rod within the intramedullary cavity can increase the risk of damage to the bone lining, and can be difficult to perform on curved bones such as the clavicle. Furthermore, apparatus heretofore known that are adapted for providing a distal anchor portion are not adapted for aligning a displaced fracture. Insertion of such devices to a misaligned fracture can cause increased separation of bone segments and possibly damage surrounding tissue. The rod's rigidity can also prevent it from centering radially when the expandable anchor portion is deployed. Such devices can therefore allow a bone to heal in a misaligned or overlapped state which can be weak or appear deformed. It would therefore be desirable to provide a intramedullary support device for use on curved bone segments that does not include a rigid internal rod portion, and which is self centering and adapted to align bone segments at a displaced fracture site.

Known IM fixation devices having an expandable anchor portion are typically constructed with a number of separate moving components. The number of moving components can make such devices expensive and susceptible to malfunction. It would be desirable to provide an IM fixation device having an expandable anchor portion which does not require a large number of separate components.

The proximal portion of known IM fixation devices is often movably disposed within the IM region of the proximal portion of a fractured clavicle bone. Such proximal portions of the device protrude from the posterior lateral end of the clavicle bone. A stabilizing nut is typically rotated to engage the threaded portion of the IM fixation device, thus causing the stabilizing nut to partially traverse the threaded portion of the IM fixation device. As the stabilizing nut traverses the threaded portion, the stabilizing nut pushes the proximal portion of the fractured clavicle bone toward the distal portion of the fractured clavicle bone. The stabilizing nut is rotated until the distal and proximal portions of the fractured clavicle bone contact each other, such that the fractured ends of the clavicle bone remain in contact with each other to allow for the accelerated healing of the clavicle fracture.

Several heretofore known IM fixation devices include portions that prominently protrude from the proximal lateral end of the clavicle bone. Even small movement of such devices can causes extreme pain to a patient. It would therefore be desirable to provide an intramedullary fixation device that does not prominently protrude externally from the bone.

Installation of some known intramedullary support devices involves invasive surgery wherein a cut-down must be performed at the fracture site. Such surgical installations increase the risk of infection, lengthen the recovery period, and often leave large unsightly scars. It would therefore be desirable to provide a method and apparatus for repairing fractured bones which is minimally invasive and which does not require a surgical cut-down at the fracture site.

Many known intramedullary support devices are not fixed within the intramedullary space and can therefore suffer from migration within the intramedullary space. It has been known for intramedullary devices or components thereof to migrate such that they pierce a patient's surrounding tissue, skin, or vital organs. It would therefore be desirable to provide an intramedullary support device that does not suffer from migration.

Many heretofore known intramedullary fixation devices are difficult to remove after a patient's fractured bone has healed. It would therefore be desirable to provide an intramedullary support device that is more easily removed from the bone after a fracture has healed.

SUMMARY OF THE INVENTION

The present invention provides a method and apparatus for minimally invasive fixation and repair of fractured long bones. The term "long bone" is used generally throughout the present specification and is meant to include any human or animal bone having sufficient intramedullary space for installation of the various embodiments of the invention described below. For example, various embodiments of the invention are described with respect to repair of a fractured collar bone in humans. It should be understood that the invention also includes a method and apparatus for repairing various other bones in humans in animals such as bones in the upper and lower extremities as well as smaller bones, including bones in human hands and fingers.

According to an illustrative embodiment of the present invention, an opening is made into the intramedullary cavity toward a proximal end of a proximal bone segment. A guide wire is inserted through the opening and pushed through the intramedullary cavity of a proximal bone segment, across the fracture site and into the intramedullary cavity of a distal bone segment. A dilator having longitudinal through-hole and a tapered leading surface is inserted over the guide wire and pushed through the intramedullary cavity into the distal bone segment to a stop at the distal end of the guide wire. The tapered leading surface of the dilator is adapted to aid in the alignment of bone segments as it is pushed across the fracture site.

A flexible tube having a radially expandable distal portion is then pushed over the guide wire into the distal bone segment and against the dilator. The expandable distal portion of the tube is deployed by compressing the flexible tube between its proximal end and the dilator. Compression of the flexible tube can be performed by threading a compression nut onto the proximal end of the guide wire. The distal stop on the guide wire prevents the dilator and flexible tube from moving further distally so that compression is applied to the flexible tube between the dilator and the compression nut. The compression nut and/or a washer disposed with the compression nut are adapted to engage the proximal bone segment so that the proximal and distal bone segments are pulled together.

One embodiment of the present invention provides a bone segment positioning apparatus including a guide wire having a proximal end and a distal end. A distal stop is disposed on the guide wire about adjacent to the guide wire distal end. A proximal stop disposed on the guide wire about adjacent to the guide wire proximal end. A tube is disposed over the guide wire. The tube has a sidewall including a radially expandable anchor portion adapted for radial expansion upon compression of the tube between the distal stop and the proximal stop.

At least one embodiment also includes a dilator having a tapered distal surface, an at least partially transverse proximal surface and a tubular inner surface defining a longitudinal through hole. The dilator is disposable on the guide wire wherein the guide wire extends through the through hole. The at least partially transverse proximal surface serves as the distal stop. In a particular embodiment, the at least partially transverse proximal surface can also be countersunk to accept the tube.

The tapered distal surface can include means to prevent rotation of the dilator relative to the guide wire. Such means can be manifest, for example in a hexagonal depression in the tapered surface that mates with a hexagonal anti-rotation feature fixed to the guide wire. For example in one embodiment, the guide wire includes a spherical distal tip having a diameter greater than the diameter of the longitudinal through hole. The means to prevent rotation in this embodiment include a polygonal mating surface of the tapered surface adapted to fit an opposite gendered polygonal mating surface of the spherical distal tip. Persons having ordinary skill in the art should appreciate that a large number of anti-rotation features such as key/slot features, interference fits, wedges and the like could be substituted as anti-rotation means within the scope of the present invention.

In one embodiment, the tube and guide wire are flexible. The proximal stop is formed as a distal surface of a compression fastener over the proximal end of the guide wire. The compression fastener comprises at least one nut threaded onto the proximal end of the guide wire. The radially expandable anchor portion includes a plurality of rib portions formed between a plurality of longitudinal slots disposed through the sidewall. The radially expandable anchor portion is disposed toward the distal end for engagement with a distal bone segment.

In an illustrative embodiment, the rib portions include at least one reduced section formed in a central portion of each rib segment. The at least one reduced section can include a crease formed transversely across the central portion of each rib segment. Alternatively the at least one reduced section comprises a narrowed section of each rib segment. The at least one reduced section could also be creased and narrowed, for example.

In a particular embodiment, the plurality of rib portions comprise at least two evenly spaced rib portions. The radially expandable anchor portion is also adapted to collapse upon relaxation of compression forces between distal and proximal segments of the tube. In another embodiment, the radially expandable anchor portion is adapted to collapse upon application of tension between distal and proximal segments of the tube.

In another embodiment, the invention provides a method for aligning fractured bone segments. The method includes installing a tube in an intramedullary space spanning a fracture, anchoring a portion of the tube to a first side of the fracture, and compressing the tube to radially expand an expandable anchor portion of the tube on a second side of the fracture.

In one embodiment, the method also includes installing a guide wire in the intramedullary space spanning the fracture. The tube is installed over the guide wire and compressed between stops on the guide wire. Anchoring a portion of the tube to a first side of the fracture can be performed, for example, by installing an anchor nut which engages the bone segment over a proximal end of the guide wire. The method can also include installing a tapered dilator over the guide wire prior to installing the tube over the guide wire. The dilator includes a transverse portion which serves as one of the stops.

In the illustrative embodiment of the invention, the method also includes drilling into the intramedullary space in a proximal bone segment; and reaming the intramedullary space. The method can also include releasing compression on the flexible tube to allow the expandable anchor portion to retract for removal of the tube and guide wire upon healing of the bone segments.

Advantages of the invention include provision of a bone segment positioning device and methodology that involves a safer, minimally invasive surgical procedure which allows for substantially less pain and discomfort for a patient. Further advantages of the invention include the ability to repair fractured bones without the need for "cut-down" at the fracture site, thus greatly reducing or eliminating any nerve and blood vessel disturbance and risk of infection. An additional advantage of the invention is that the bone segment positioning device is easily removable and malleable. The malleability of the device adds an extra degree of safety because the device will bend rather than applying potentially damaging lateral pressures in the IM cavity.

The present invention overcomes the deficiencies of the prior art by providing a clavicle repair apparatus with reduced risk of injury to the subclavian artery. An intramedullary apparatus is provided that is suitable for use in curved bone segments without presenting a high risk of damaging surrounding tissue. The various embodiments of the present invention also provide an intramedullary support device for use on curved bone segments that does not include a rigid internal rod portion, and which is self centering and adapted to align bone segments at a displaced fracture site.

Further, the present invention provides an IM fixation device having an expandable anchor portion which does not require a large number of separate components and does not prominently protrude externally from the bone. The various embodiments of the present invention also provide a method and apparatus for repairing fractured bones which is minimally invasive and which does not require a surgical cut-down at the fracture site

BRIEF DESCRIPTION OF DRAWINGS

The foregoing and other features and advantages of the present invention will be better understood from the following detailed description of illustrative embodiments, taken in conjunction with the accompanying drawings in which.

DETAILED DESCRIPTION OF THE INVENTION

Figure 1:
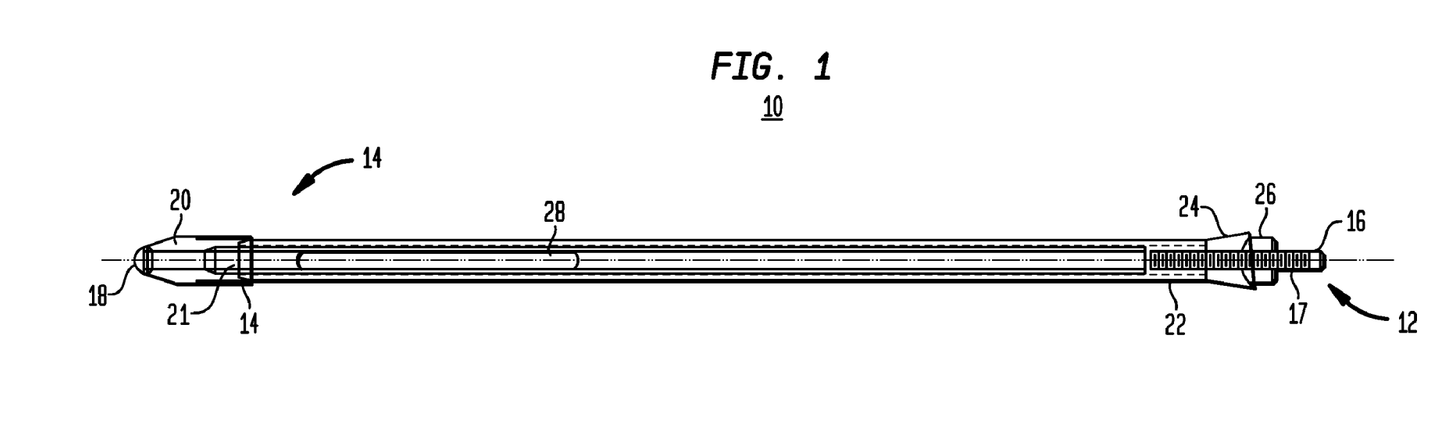
FIG. 1 is a side cross sectional view of a long bone compression apparatus according to an illustrative embodiment of the present invention.

In FIG. 1, the components of a long bone compression apparatus 10 having a proximal end 12 and a distal end 14 according to the an illustrative embodiment of the invention are shown assembled together in a cross sectional view. A guide wire 16 extends from the distal end 14 to the proximal end 12 of the compression apparatus and includes a threaded portion 17 on the proximal end of the guide wire 16 and a distal end stop 18 disposed on the distal end of the guide wire 16. A dilator 20 is disposed over the guide wire 16 adjacent to the distal end stop 18. As disclosed herein, the term 'distal' refers to the element or portion furthest from the threaded portion 17 of the guide wire 16 and the term 'proximal' refers to the element or portion closest to the threaded portion 17 of the guide wire 16.

In the embodiment shown in FIG. 1, an inner tube 21 is disposed over the guide wire 16 and an outer tube 22 is disposed over the inner tube 21. Both the inner tube 21 and outer tube 22 abut the dilator 20. An interface washer 24 is disposed over the threaded portion of the guide wire and abuts the proximal end of the outer tube 22. A nut 26 is threaded onto the threaded portion 17 of the guide wire 17 and abuts the interface washer 24. At least one slot 28 extends through the outer tube 22.

Figure 2:
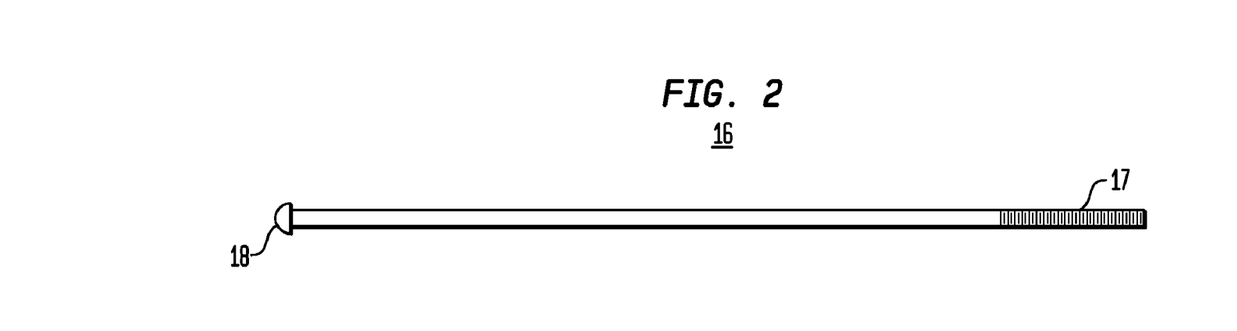
FIG. 2 is a plan view of a guide wire according to an illustrative embodiment of the present invention.

In FIG. 2, an illustrative embodiment of a guide wire 16 according to the present invention is shown. The guide wire 16 includes a distal end stop 18. The end stop 18 can be formed integrally with the guide wire 16 or can be a separate component assembled securely thereto. In the embodiment of FIG. 2, the end stop has a spherical shape. Persons skilled in the art should appreciate that the end stop could be made in virtually any shaped radial protrusion of sufficient length formed with or fixed to the distal end of the guide wire. The end stop 18 must extend radially beyond the outside surface of the guide wire by a distance greater than the diameter of a through hole in the dilator 20 through which the guide wire passes.

In at least one embodiment of the invention, the end stop 18 includes anti-rotation surfaces such as a hexagonal outside surface for mating with a hexagonal cavity in the dilator. In another embodiment, the end stop 18 can be formed as a T shape at the distal end of the guide wire. The T shaped end stop can prevent rotation of the dilator 20 relative to the guide wire 16 if a dilator 20 having a mating slot in its distal portion which accepts the T shaped end stop.

The proximal end of the guide wire has a threaded exterior surface for engagement with a compression nut. In the illustrative embodiment the threads are a 0-80 UNF thread extending 0.620 inches from the proximal end of the guide wire. Persons skilled in the art should appreciate that a number of different thread sizes could be substituted for engagement with a compression nut according to the present invention and that the threads can extend along a length shorter or longer than the length shown in FIG. 2. It is envisioned, for example, that an alternative embodiment of the invention could be constructed using a guide wire having a threaded surface along its entire length.

In the illustrative embodiment, the guide wire has a circular cross section and is made from TI6AL-4AV ELI Alloy per ASTM F160. Persons skilled in the art should appreciate that the guide wire could alternatively be made from a number of clinically suitable materials such as stainless steel, molded or extruded polymers and the like. It is envisioned that a guide wires having a different cross sectional geometry can also be used in alternative embodiments of the invention. For example, it is envisioned that a flat steel band could be substituted for a circular cross sectional guide wire in alternative embodiments of the invention. Although the guide wire is described herein generally in terms of a flexible wire, persons skilled in the art should appreciate that the guide wire can be made from a flexible rod or elongated flexible structure.

Figure 3:
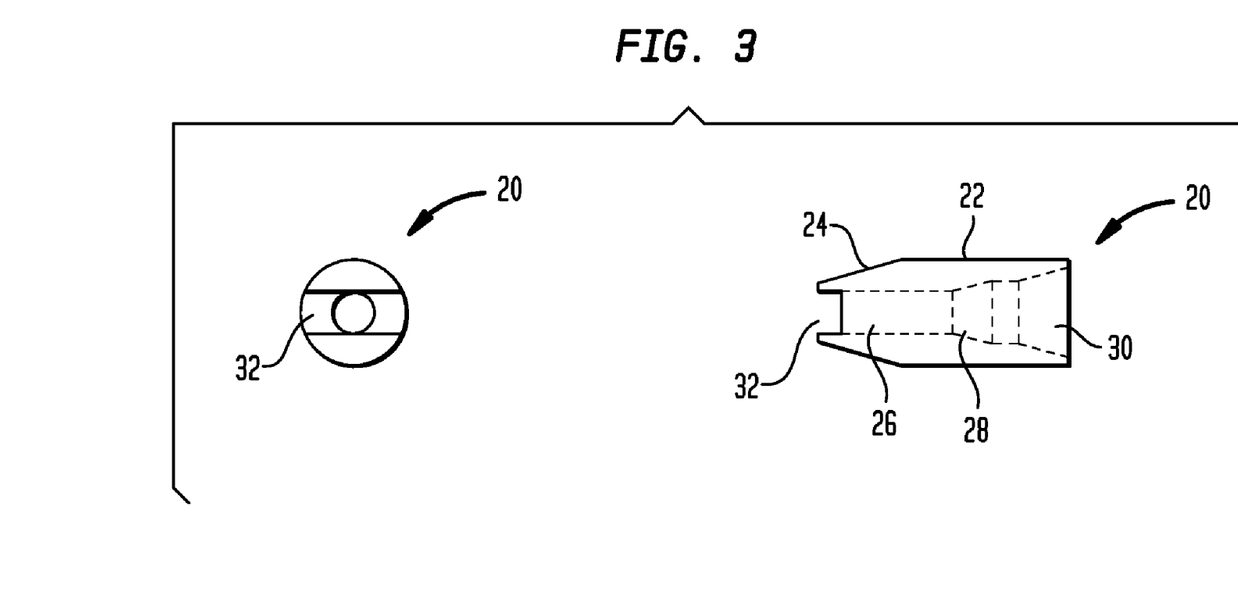
FIG. 3 is a cross sectional view of a dilator according to an illustrative embodiment of the present invention.

In FIG. 3, an illustrative embodiment of a dilator 20 according to the present invention is shown. In the illustrative embodiment, the dilator 20 has a circular cylindrical body portion 22 and a tapered distal portion 24. A cylindrical through hole 26 extends through the center of the dilator along its longitudinal axis. The through hole diameter is greater than the diameter of the guide wire to facilitate travel of the dilator along the guide wire up to the distal end stop of the guide wire.

The dilator 20 can also include one or more counter bores in its proximal end to accept one or more tubes disposed over the guide wire. In the embodiment shown in FIG. 3, the dilator 20 includes an inner counter bore 28 for accepting an inner tube disposed over the guide wire 16 and an outer counter bore 30 for accepting an outer tube disposed over the guide wire 16. In the illustrative embodiment, the counter bores include tapered portions adapted for mating with tapered distal ends of a respective tube.

In the embodiment shown in FIG. 3, the dilator 20 includes a transverse slot 32 extending across its tapered distal portion 24. The slot 32 is adapted to accept an anti-rotation surface of the guide wire end stop 18. In the illustrative embodiment, the dilator 20 is made from TI6AL-4V ELI Alloy per ASTM F133. Persons skilled in the art should appreciate that a number of alternative materials could alternatively be used to fabricate a dilator 20 according to the present invention. For example, stainless steel or medically suitable polymers and the like can be used to fabricate a dilator 20 within the scope of the present invention In FIG. 4, an inner tube 21 as used in a particular embodiment of the present invention is shown. The inner tube 21 has a tapered distal end 34 for engagement with the inner counter bore 28 (FIG. 3) in the dilator 20. An internal cavity 36 adapted for sliding over the guide wire 16 extends along the full length of the inner tube 21 along its longitudinal axis. Alternatively, it is envisioned that the invention could also be practiced using a guide wire and inner tube that are engaged by threading one with the other. In such an embodiment a threaded internal cavity is adapted for threading onto a threaded guide wire.

Figure 4:
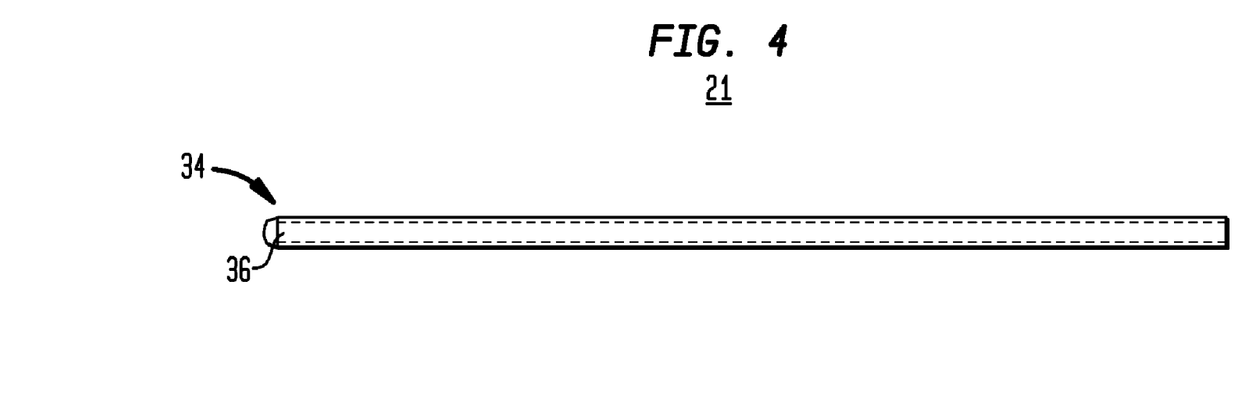
FIG. 4 is a cross sectional view of an inner tube according to an illustrative embodiment of the present invention.

In the illustrative embodiment shown in FIG. 4, the inner tube 21 is made from nitinol tubing having a 0.090" outside diameter and a 0.062" inside diameter. Nitinol is a particularly suitable material for use in components of an IM fixation device because it has stress/strain characteristics that approximate the stress/strain characteristic of human and animal bones. Persons skilled in the art should appreciate that a number of different materials could be used having a number of different inside and outside diameters to substitute for the illustrative inner tube 21 within the scope of the present invention.

Since a function of the inner tube 21 in an illustrative embodiment is to push the dilator 20 along the guide wire 16 to the distal stop 18, inner tube material and inner tube dimensions of such embodiments should have sufficient rigidity to force the dilator 20 along the guide wire 16 even when resistance is presented by friction in the IM cavity, for example when the dilator traverses a misaligned fracture site. In embodiments of the invention intended for use in curved long bones, the inner tube 21 should be sufficiently flexible to travel around curves in the IM cavity of the curved bone. Although the various embodiments of the invention are described herein as having an inner tube 21 with a generally circular cross-section, persons skilled in the art should appreciate that an inner tube having a different cross-sectional shape, such as for example, an oval or polygon could be substituted therefore without departing from the spirit and scope of the invention.

Figure 5:
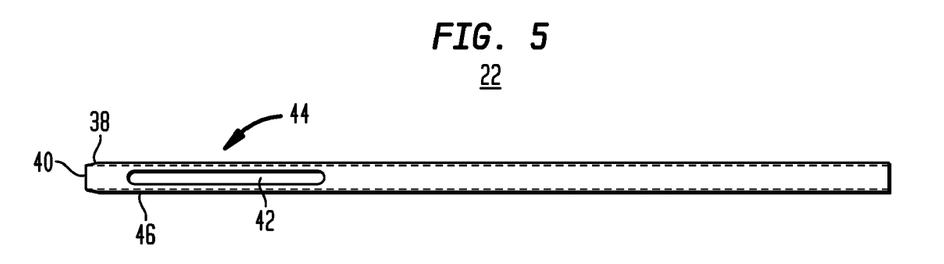
FIG. 5 is a cross sectional view of an outer tube according to an illustrative embodiment of the present invention.

In FIG. 5, an illustrative embodiment of an outer tube according to the present invention is shown. The outer tube 22 has a tapered distal end 38 for engagement with the outer counter bore of the dilator 20. Alternative embodiments of the invention can be practiced using an outer tube 22 without a tapered distal end. For example, persons skilled in the art should appreciate that certain embodiments of the present invention can be practiced without any counter bore in the dilator 20. In these and other alternative embodiments, an outer tube 22 having a non-tapered distal end can be used.

An internal cavity 40 adapted for sliding over the inner tube 21 extends along the full length of the outer tube 22 along its longitudinal axis. Persons skilled in the art should appreciate that the internal cavity 40 could alternatively be threaded for engagement with an inner tube 21 having a threaded outer surface. In other alternative embodiments of the present invention no inner tube 21 is used. In such embodiments, the internal cavity 40 of the outer tube 22 is adapted for sliding over or threading over the guide wire.

In the embodiment shown in FIG. 5, the outer tube 22 is made from nitinol tubing having a 0.140" outside diameter and a 0.105" inside diameter. Persons skilled in the art should appreciate that a number of different materials could be used having a number of different inside and outside diameters to substitute for the illustrative inner tube 21 within the scope of the present invention. In embodiments of the invention intended for use in curved long bones, the outer tube 22 should be sufficiently flexible to travel around curves in the IM cavity of the curved bone. Although the various embodiments of the invention are described herein as having an outer tube 22 with a generally circular cross-section, persons skilled in the art should appreciate that an inner tube having a different cross-sectional shape, such as for example, an oval or polygon could be substituted therefore without departing from the spirit and scope of the invention.

At least one slot 42 defines an anchor portion of the outer tube. In the illustrative embodiment, four slots having uniform annular spacing extend through the outer tube toward the proximal end of the tubing to define the anchor portion 44. The four slots 42 define four ribs 46 therebetween which are designed to collapse radially outward upon compression of the outer tube between its ends. In an illustrative embodiment of the invention, the four ribs are also designed to regain their approximate original shape upon relaxation of the compressive force.

In the illustrative embodiment shown in FIG. 5, the slots are 1" long and 0.062" wide having a full radius at either end. Persons skilled in the art should appreciate that various rib dimensions by the various slot dimensions and various numbers of ribs and slots can be used in alternative embodiments of the present invention. It should be understood that the rib 46 and slot 42 dimensions are critical to the functionality of the anchor portion 44 and will depend upon the mechanical properties of the material used for fabricating the outer tube and the thickness of the outer tube wall.

In other alternative embodiments of the present invention slots between the ribs 46 of the anchor portion 44 are shaped to define a folding location on the rib 46. For example the slots 42 can have a wider section at the midpoint of their length to create a narrower portion of each rib 46 formed between two such slots 42. The narrower portion of such ribs 46 at the midpoint of their length can provide a folding location on the rib 46. Other structures that could be used to create a folding location include an internal annular groove, an external annular groove, a perforation, an embossment or the like. It is envisioned that in still another embodiment of the present invention, a folding portion can be formed by dividing ribs 46 at the folding location and installing a hinges between rib segments.

It is envisioned that alternative embodiments of the invention will include gripping portions (not shown) configured on one or more of the ribs 46 to provide increased friction between the anchor portion 44 and the intramedullary wall. For example, it is envisioned that alternative embodiments of the invention will include textured rib portions, serrated rib portions and the like for improved engagement with the intramedullary wall when the anchor portion 44 is deployed.

Although the various embodiments of the invention are described herein in terms of a single anchor portion 44, it is envisioned that alternative embodiments of the invention will be practiced using more than one anchor portion 44 disposed along the outer tube 22. In alternative embodiments, it is envisioned that the additional anchor portions (not shown) can be configured with different dimensions to cause a specific sequence of engagement upon application of compressive forces to the outer tube 22.

Figure 6:
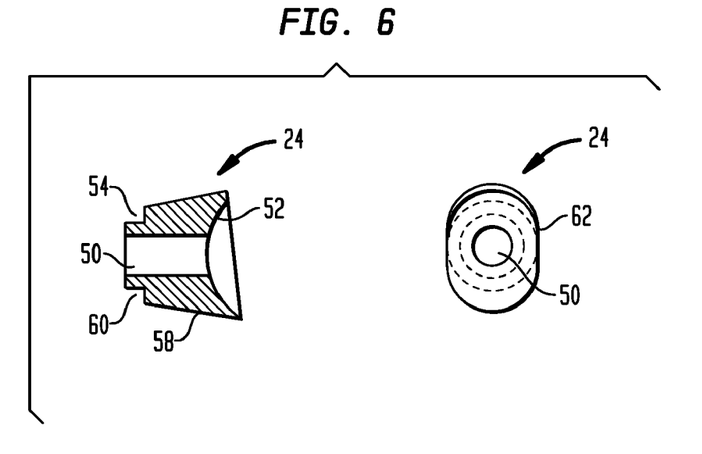
FIG. 6 is a cross sectional view of an interface washer according to an illustrative embodiment of the present invention.
Figure 7:
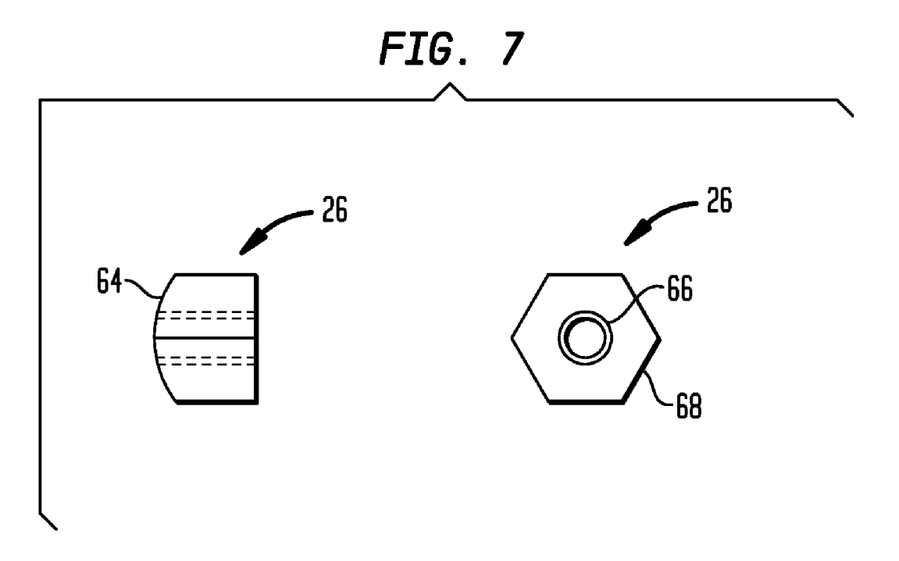
FIG. 7 is a cross sectional view of a compression nut according to an illustrative embodiment of the present invention.

In FIG. 6, an interface washer 24 according to an illustrative embodiment of the present invention is shown. The interface washer includes a through hole 50 extending along its longitudinal axis. The through hole 50 is adapted to fit over the guide wire 16. In an alternative embodiment the through hole 50 of the interface washer 24 can be threaded for threading engagement to a threaded portion of the guide wire 16. A concave proximal surface 52 is adapted for alignment with a convex distal surface 64 of a compression nut 26 (FIG. 7).

Persons skilled in the art should appreciate that alternative embodiments of the present invention can be practiced by providing a convex proximal surface on the interface washer 24 and a concave distal surface on the compression nut 26 without including a concave or convex proximal surface in the interface washer 24 and/or compression nut 26. For example, it is envisioned that an interface washer having a flat proximal surface can be used with a flat compression nut without providing any alignment between the compression nut and interface washer. Alternatively a number of different surface combinations can be used to provide alignment between the interface washer and the compression nut while allowing relative rotation therebetween.

In the illustrative embodiment shown in FIGS. 1 and 6, a step 54 is formed between a first outside diameter 56 adapted for fitting to the inside diameter of the outer tube 22 and a bone interface surface 58. The step 54 defines a compression surface 60 which abuts the proximal end of the outer tube 22. In the illustrative embodiment, the bone interface surface 58 is tapered outward in the proximal direction. The bone interface surface 58 engages a proximal bone segment by being pressed into a hole drilled in the proximal segment when a compression nut 26 is threaded to the guide wire 16. The outward tapering of the bone interface surface 58 in the illustrative embodiment allows the washer to be partially inserted into a drilled entry hole in a proximal bone segment to secure the proximal end of the apparatus 10 (FIG. 1) to the proximal bone segment.

Persons skilled in the art should appreciate that the present invention can be practiced using a number of different types of bone interface surfaces. For example, it is envisioned that a stepped surface having serrations could be used as a bone interface surface in an alternative embodiment of an interface washer according to the present invention. In the alternative embodiment, the stepped surface would include a first surface fitting into the drilled entry hole and the step surface wider than the drilled entry hole having serrations for engaging the outside of the proximal bone.

Flat portions 62 are provided on the surface of the interface washer 24 for engagement with an anti-rotation tool such as a wrench. In the illustrative embodiment shown in FIG. 6, a pair of parallel flat portions 62 are suitable for engagement with a wrench, pliers or other anti-rotation tool. Persons skilled in the art should appreciate that a number of different surface configurations can be provided on the interface washer to prevent rotation of the washer while the compression nut is installed. For example, the pair of flat portions 62 can be replaced by a hexagonal or other polygonal surface adapted for engagement by a wrench or a knurled surface adapted for being gripped by hand. Alternatively, it is envisioned that one or more radial arms could be provide extending from the proximal portion of the interface washer 24 for gripping to prevent rotation of the interface washer 24 when the compression nut 26 is installed.

In the illustrative embodiment, the interface washer is made from TI6AL-4V ELI ALLOY PER ASTM F136. Persons skilled in the art should appreciate that an interface washer 24 according to the invention could alternatively be made from a number of different clinically suitable materials such as stainless steel, thermoplastic or the like.

In FIG. 7, a compression nut 26 according to the present invention is shown. The compression nut 26 includes a convex distal surface 64 adapted for alignment in the concave proximal surface 52 of the interface washer 24. A threaded through hole 66 extends along the longitudinal axis of the compression nut 26. The threaded through hole is adapted for threading onto the threaded portion of the guide wire. Flat surfaces are provided for engagement with a rotation tool such as a wrench, nut driver, pliers or the like.

Persons skilled in the art should appreciate that a number of different shaped tool engagement surfaces may be provided on the compression nut 26 for engaging a tool adapted to the particular shape for threading the compression nut 26 on the guide wire 16. It is also envisioned that the flat surfaces 68 can be replaced by a knurled surface adapted for being gripped by hand. Alternatively, it is envisioned that one or more radial arms could be provide extending from the compression nut 26 to aid in manual threading of the compression nut onto the guide wire 16.

In the illustrative embodiment shown in FIG. 7 the compression nut is made from TI6AL-4V ELI ALLOY PER ASTM F136. Persons skilled in the art should appreciate that a compression nut 26 according to the invention could alternatively be made from a number of different clinically suitable materials such as stainless steel, thermoplastic or the like.

Figure 8:
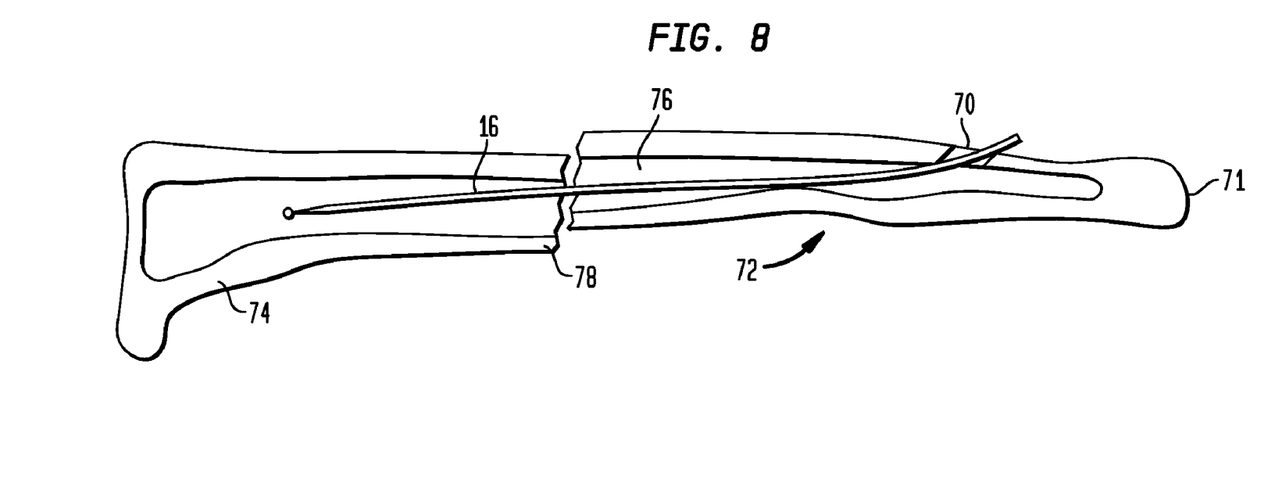
FIG. 8 is a cross sectional view of a fractured long bone illustrating the method of inserting a guide wire according to an illustrative embodiment of the present invention.

A method of using the present invention will be described first with respect to FIGS. 8-12. It should be understood by persons skilled in the art that the methods of installing the present invention can be best performed using imaging technology such as fluoroscopic imaging techniques, ultrasonic imaging or the like to monitor positions of the various components of the apparatus during installation. As shown in FIG. 8, a hole 70 is drilled through the bone wall 71 into the IM cavity 76 toward the proximal end of a proximal bone segment 72 of a fractured bone. It should be understood the in the context of this disclosure the terms broken and fractured used in conjunction with a bone includes but is not limited to greenstick fractures, displace fractures, plastic deformity, torus (buckle) fractures, growth plate fractures, closed fractures, open (compound) fractures, comminuted fractures, pathological fractures, stress fractures and the like.

The hole 70 must be wide enough to allow passage of the dilator 20, guide wire 16, outer tube 22 and (optionally) inner tube 21 but narrow enough to engage the bone interface washer 24 of the apparatus 10.

Figure 13:
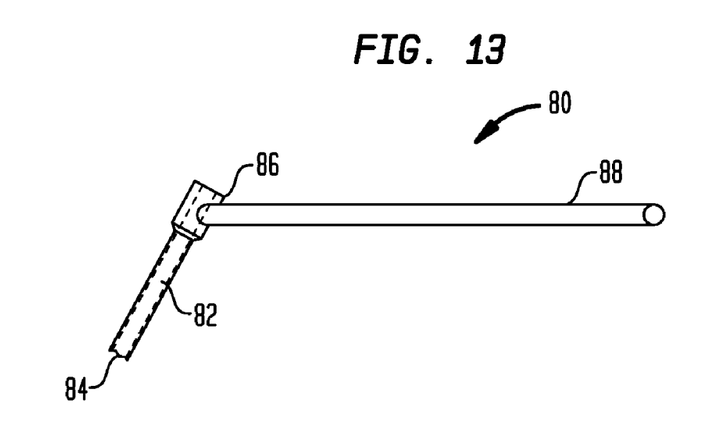
FIG. 13 is a cross sectional view of a drill guide suitable for use in methods of installing the intramedullary device according to the present invention.

In at least one embodiment of the invention a drill guide is used to align a drill bit at a constant orientation relative to the bone while drilling and to prevent the drill bit from drilling beyond the IM cavity. An exemplary drill guide 80 for use in the illustrative method of installing intramedullary support apparatus 10 of the present invention is shown in FIG. 13. The drill guide includes a hollow shaft 82 adapted for guiding a drill bit. The hollow shaft has a bone engagement surface 84 which can include features such as serrations to prevent slippage on the exterior surface of a bone. The hollow shaft also has a drill stop surface 86 displaced from the bone engagement surface 84 by a distance determined to allow a drill bit to enter the IM cavity but to prevent the drill bit from drilling beyond the IM cavity. A handle 88 extending from the shaft 82 allows the drill guide to be securely held in place during a drilling procedure.

Once the hole is drilled, a guide wire 16 is inserted into the IM cavity and manually pushed across the fracture site 78 into the distal bone segment 74. The proximal portion of the guide wire 16 remains extending outside of the drilled hole 70. A dilator 20 is installed over the proximal end of the guide wire 16 and pushed into the IM cavity 76, across the fracture site 78 and into the IM cavity 76 of the distal bone segment 76.

Figure 9:
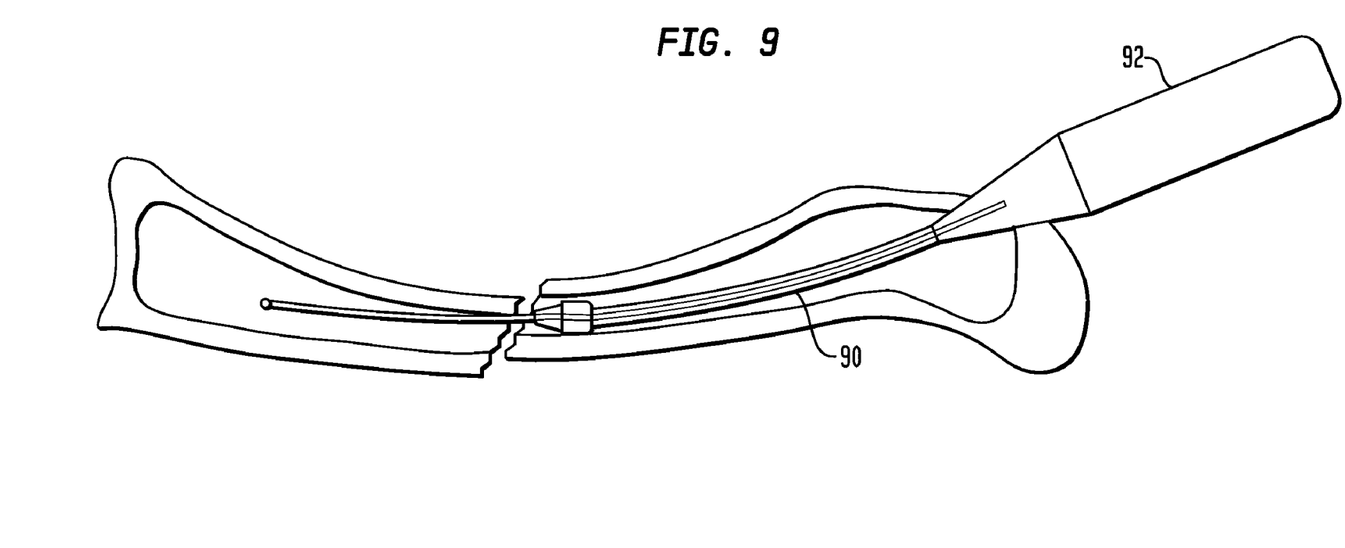
FIG. 9 is a cross sectional view of a fractured long bone illustrating a method of installing a dilator according to an illustrative embodiment of the present invention.
Figure 10:
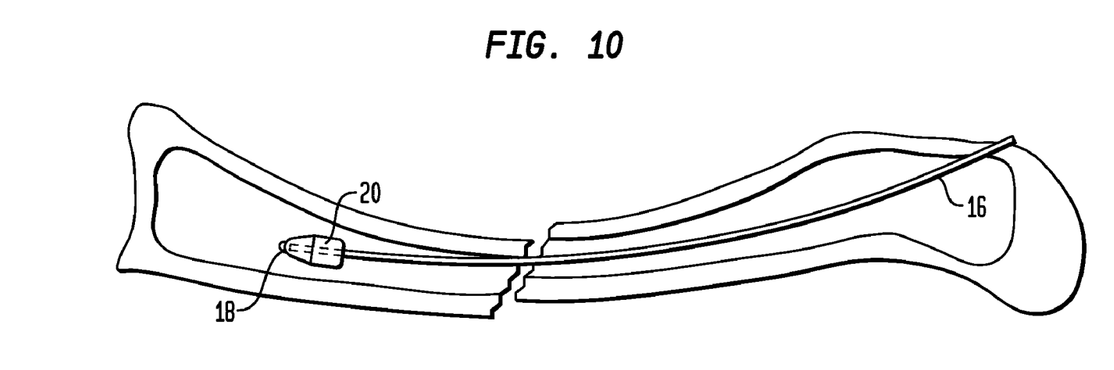
FIG. 10 is a cross sectional view of a fractured bone segment having a guide wire and a dilator installed according to an illustrative embodiment of the present invention.

In at least one embodiment of the invention, as shown in FIG. 9, a flexible tube is used to push a dilator along the guide wire. A handle 92 can be used to allow better gripping leverage to manually push the flexible tube 90 from the proximal end. As the tapered distal portion of the dilator crosses a fracture site, the tapered surface engages the bone wall of the distal bone segment and tends to align the fractured bone segments with each other. As shown in FIG. 10, the dilator is pushed to the end stop disposed on the distal end of the guide wire. In this illustrative embodiment the flexible tube is removed once the dilator reaches the end stop.

In an alternative embodiment, using an inner tube 21, the inner tube is used to push the dilator through the IM cavity. The inner tube 21 is then left in place and becomes part of the bone fixation apparatus 10.

Figure 11:
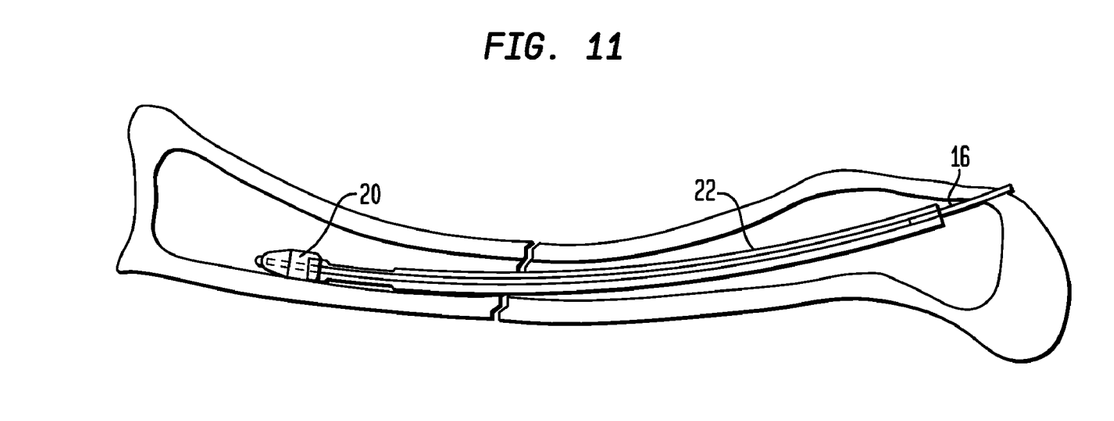
FIG. 11 is a cross sectional view of a fractured bone segment having a guide wire, dilator and outer tube installed in the intramedullary cavity according to an illustrative embodiment of the present invention.

Next, as shown in FIG. 11, an outer tube 22 is installed by pushing the outer tube over the guide wire (and over the inner tube 21 if an inner tube is installed). The outer tube is pushed as far as possible until it is stopped by the proximal surface of the dilator 20.

Once the outer tube 22 is fully installed, a bone interface washer is installed over the proximal end of the guide wire 16. A compression nut is then placed over the proximal end of the guide wire and threaded along the threaded portion of the guide wire. In the illustrative embodiment, the bone interface washer is wedged into the hole and held fixed while the compression nut is turned. When the compression nut reaches is prevented from traveling distally by the compression nut, further threading of the nut causes the nut to pull the guide wire in the proximal direction.

Figure 12:
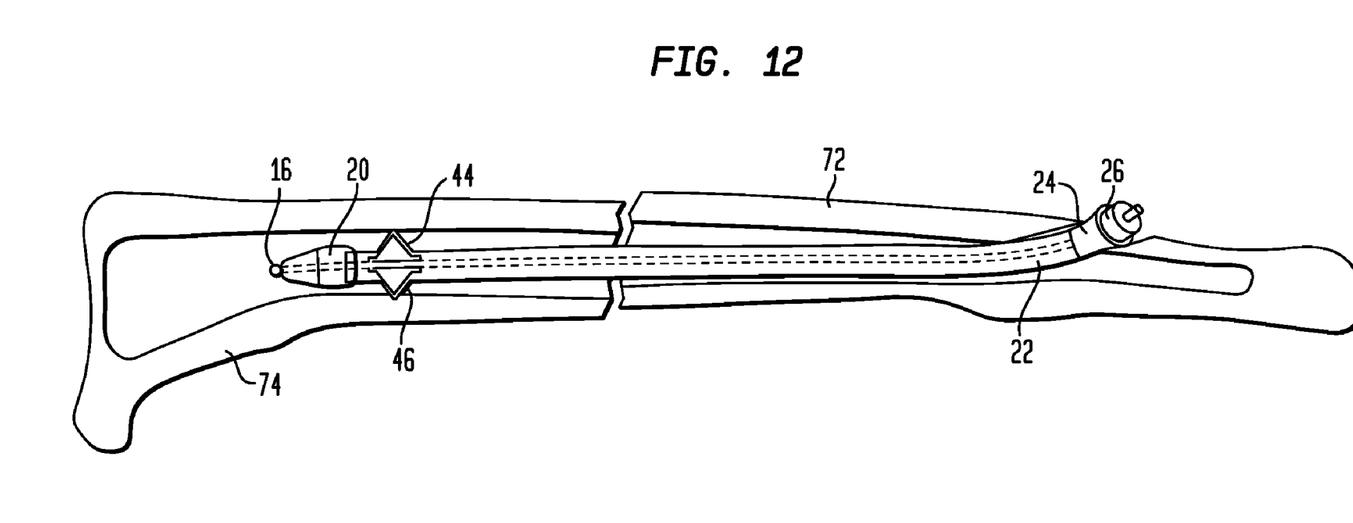
FIG. 12 is a cross sectional view of a fractured long bone having an intramedullary fixation apparatus according to an illustrative embodiment of the present invention installed therein with an expanded anchor portion.

While the proximal end of the outer tube 22 is prevented from moving distally by the bone interface washer 24, the distal end of the outer tube is pulled proximally by the guide wire 16 and dilator 20. The outer tube 22 is thereby subject to a compressive force which causes the anchor portion 44 to deploy i.e. as the ribs 46 of the outer tube i.e. fold radially outward (FIG. 12). Once the anchor portion 44 deploys, it engages the inner surface of the bone (i.e. the outer wall of the IM cavity) in the distal bone segment. Further turning the compression nut 26 causes the engaged distal bone segment 74 to be pulled against the proximal bone segment 72 thereby securing the fracture site under a compressive force.

In the alternative embodiment of the invention having an inner tube 21 (FIG. 4) disposed over the guide wire 16, the inner tube 21 can have a length relative to the length of the outer tube adapted so that the inner tube abuts the bone interface nut when an optimal anchor deployment condition is reached or to stop excessive advancement of the compression nut 26. In another alternative embodiment, the threaded portion 17 of the guide wire 16 extends only long enough along the guide wire 16 to allow optimal advancement of the compression nut 26 and thereby cause optimal engagement of the anchor portion 44.

Figure 14:
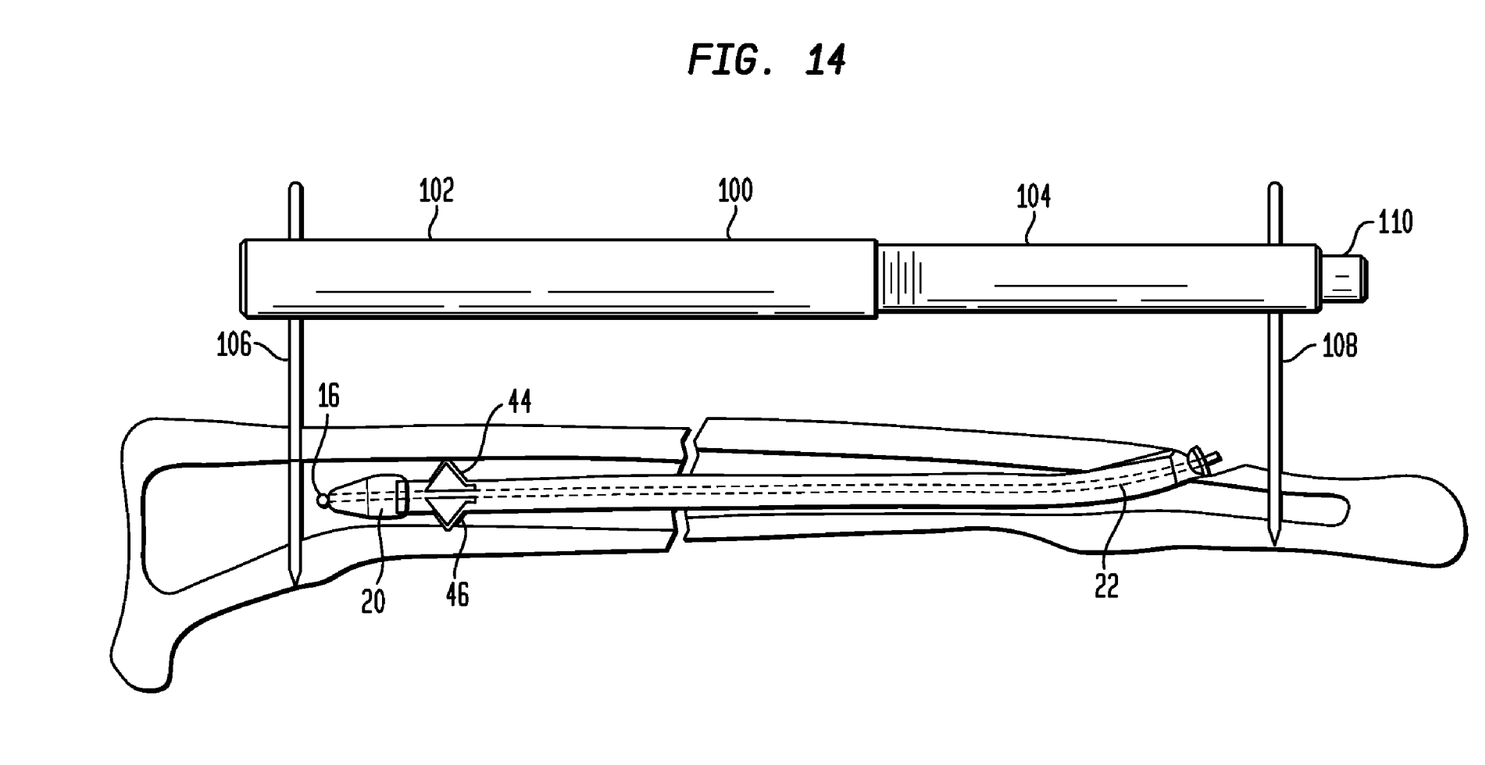
FIG. 14 is a cross sectional view of a fractured long bone having an intramedullary fixation apparatus installed therein and illustrating the use of an external fixation device in conjunction with the intramedullary fixation apparatus according to an illustrative embodiment of the present invention.

In an alternative method of installing the apparatus according to the present invention, an external reduction device is used to hold bone segments in place while the IM device 10 is installed. As shown in FIG. 14, the external fixation device includes a pair of telescoping tubes 102, 104 and a pin 106, 108 extending from the end of each telescoping tube 102, 104 into a respective bone segment. The pins 106, 108 are installed in holes drilled in each bone segment using fluoroscopic imaging as known in the art. An adjustment nut 110 causes the telescoping tubes 102, 104 to translate toward each other causing a compressive force between the bone segments. The external reduction apparatus 100 is left in place during installation of the IM bone fixation apparatus 10 of the invention and removed once the IM bone fixation apparatus 10 is in place.

In embodiments of the invention intended for use in to repair curved bones, it should be understood by persons skilled in the art that the guide wire 16, inner tube 21, and outer tube 22 should have sufficient flexibility to allow each of these components to be installed sequentially in the IM space the curved bones. Once installed the combined strength and rigidity of these components provide the structure necessary for maintaining compression and providing strength to the bone under repair.

Figure 15:
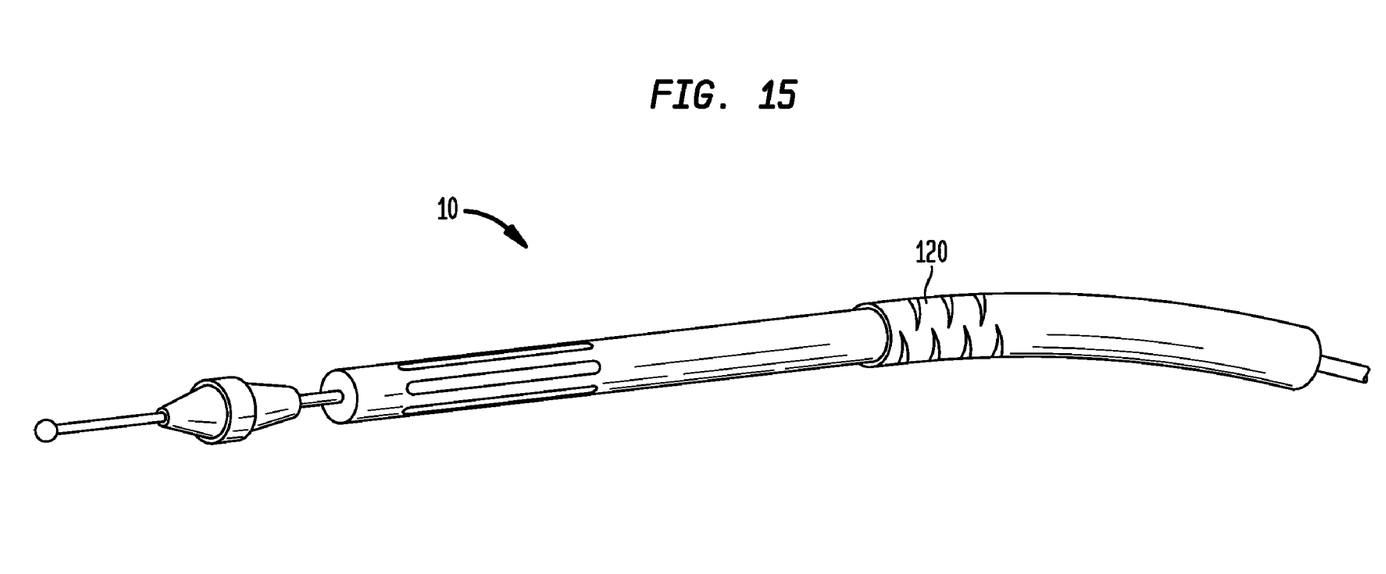
FIG. 15 is a pictorial view of a partially assembled intramedullary fixation apparatus according to an alternative embodiment of the invention including an outer tube having a plurality of semi-annular cuts.

In an alternative embodiment of the invention shown in FIG. 15, one or more semi-annular 120 cuts are provided in the outer tube 22 to increase flexibility for installation in the IM space curved bones. Such semi-annular cuts 120 increase flexibility in the outer tube 22 while maintaining strength in compression that is necessary to cause deployment of the anchor portion 44. Persons skilled in the art should appreciate that various similar structures can be substituted for the semi-annular cuts 120 according to the alternative embodiment within the scope of the present invention.

It is completed in the practice of this invention that, in particular embodiments, the devices of this invention will be coated, in whole or in part, with bioactive material. As used herein bioactive material shall be broadly construed to include, without limitation, immunomodulators such as a cyclosporine, anti infectives such as antiviral or antibiotic compounds, angiogenic or antiangiogenic compounds, growth factors, antineoplastics compounds, compounds to encourage or prevent the adherence (or infiltration) of the device to the surrounding tissue, and other therapeutic agents. Further included are coatings to improve detection of the device such as radiopaque coatings and contrast media. Further contemplated are biodegradable coatings and coatings which may be impregnated with bioactive agents.

While the invention has been described with reference to an exemplary embodiment, it should be understood by those skilled in the art that various changes, omissions and/or additions may be made and equivalents may be substituted for elements thereof without departing from the spirit and scope of the invention. In addition, many modifications may be made to adapt a particular situation or material to the teachings of the invention without departing from the scope thereof. Therefore, it is intended that the invention not be limited to the particular embodiment disclosed for carrying out this invention, but that the invention will include all embodiments falling within the scope of the appended claims. The teaching of all references cited herein are incorporated herein by reference.

What is claimed is:

1. An intermedullary apparatus for positioning and providing compressive fixation of fractured bones comprising:
   a guide wire having a proximal end and a distal end;
   a dilator disposed on said guide wire about adjacent to said guide wire distal end;
   a proximal stop disposed on said guide wire about adjacent to said guide wire proximal end;
   said dilator having a tapered distal surface, an at least partially transverse proximal surface and a tubular inner surface defining a longitudinal through hole, said dilator being disposable on said guide wire wherein said guide wire extends into said through hole;
   a tube disposable over said guide wire and having a sidewall including a radially expandable anchor portion adapted for radial expansion upon compression of said tube between said at least partially transverse proximal surface and said proximal stop; and
   wherein said tapered distal surface includes means to prevent rotation of said dilator relative to said guide wire.

2. The apparatus according to claim 1 wherein said guide wire includes a distal tip having a diameter greater than the diameter of said longitudinal through hole.

3. The apparatus according to claim 2 wherein said means to prevent rotation comprise a polygonal mating surface adapted to fit an opposite gendered polygonal mating surface of said distal tip.

4. An intermedullary apparatus for positioning and providing compressive fixation of fractured bones comprising:
   a guide wire having a proximal end and a distal end;
   a dilator disposed on said guide wire about adjacent to said guide wire distal end;
   a proximal stop disposed on said guide wire about adjacent to said guide wire proximal end;
   said dilator having a tapered distal surface, an at least partially transverse proximal surface and a tubular inner surface defining a longitudinal through hole, said dilator being disposable on said guide wire wherein said guide wire extends into said through hole;
   a tube disposable over said guide wire and having a sidewall including a radially expandable anchor portion adapted for radial expansion upon compression of said tube between said at least partially transverse proximal surface and said proximal stop;
   wherein said tube and said guide wire are flexible; and
   wherein said ribs include at least one reduced section formed in a central portion of each rib.

5. The apparatus according to claim 4 wherein said at least one reduced section comprises a crease formed transversely across said central portion of each rib.

6. The apparatus according to claim 4 wherein said at least one reduced section comprises a narrowed section of each rib.

7. A long bone segment positioning apparatus comprising:
   a flexible guide wire having a proximal end and a distal end;
   a distal stop disposed on said guide wire about adjacent to said guide wire distal end;
   a proximal stop disposed on said guide wire about adjacent to said guide wire proximal end;
   a flexible tube disposable over said guide wire and having a sidewall including a radially expandable anchor portion adapted for radial expansion upon compression of said tube between said distal stop and said proximal stop;
   a dilator having a tapered distal surface, an at least partially transverse proximal surface and a tubular inner surface defining a longitudinal through hole; said dilator being disposable on said guide wire wherein said guide wire extends through said through hole;
   wherein said at least partially transverse proximal surface is countersunk to accept said tube and serves as said distal stop;
   wherein said distal stop has a width greater than the diameter of said longitudinal through hole;
   wherein said proximal stop is formed as a distal surface of an interface washer installed over said proximal end of said guide wire;
   wherein said radially expandable anchor portion comprises a plurality of evenly spaced ribs formed between a plurality of longitudinal slots disposed through said sidewall;
   wherein said radially expandable anchor portion is disposed toward said distal end for engagement with a distal bone segment;
   wherein said ribs include at least one reduced section formed in a central portion of each rib segment; and
   wherein said radially expandable anchor portion is adapted to collapse upon relaxation of compression forces between distal and proximal segments of said tube.

* * * * *